United States Patent
Roos et al.

(10) Patent No.: US 7,015,043 B2
(45) Date of Patent: Mar. 21, 2006

(54) FLOW CELL METHOD

(75) Inventors: Håkan Roos, Uppsala (SE); Kjell Magnusson, Uppsala (SE); Mattias Tidare, Uppsala (SE)

(73) Assignee: Biacore AB, Uppsala (SE)

( * ) Notice: Subject to any disclaimer, the term of this patent is extended or adjusted under 35 U.S.C. 154(b) by 731 days.

(21) Appl. No.: 10/184,024

(22) Filed: Jun. 26, 2002

(65) Prior Publication Data

US 2003/0022388 A1   Jan. 30, 2003

Related U.S. Application Data

(60) Provisional application No. 60/301,898, filed on Jun. 29, 2001.

(30) Foreign Application Priority Data

Jun. 29, 2001   (SE)   .................................... 0102331

(51) Int. Cl.
*G01N 1/10* (2006.01)
*G01N 21/05* (2006.01)

(52) U.S. Cl. ..................... 436/53; 436/164; 436/166; 422/82.05; 422/100

(58) Field of Classification Search ................ 436/43, 436/52, 164, 166, 172, 174, 180; 422/81, 422/100, 82.05, 82.09, 82.11
See application file for complete search history.

(56) References Cited

U.S. PATENT DOCUMENTS

| | | | |
|---|---|---|---|
| 4,056,324 A  * | 11/1977 | Gohde | 356/246 |
| 5,242,828 A | 9/1993 | Bergström et al. | 435/291 |
| 5,313,264 A | 5/1994 | Ivarsson et al. | 356/73 |
| 5,436,161 A | 7/1995 | Bergström et al. | 435/291 |
| 5,492,840 A | 2/1996 | Malmqvist et al. | 436/518 |
| 5,773,298 A  * | 6/1998 | Lynggaard et al. | 436/52 |
| 6,087,705 A  * | 7/2000 | Gardner et al. | 257/510 |
| 6,170,981 B1 * | 1/2001 | Regnier et al. | 366/336 |
| 6,200,814 B1 * | 3/2001 | Malmqvist et al. | 436/52 |
| 6,905,029 B1 * | 6/2005 | Flagan | 209/210 |
| 2003/0226806 A1* | 12/2003 | Young et al. | 210/634 |

FOREIGN PATENT DOCUMENTS

| | | |
|---|---|---|
| WO | WO 90/05245 | 5/1990 |
| WO | WO 90/05305 | 5/1990 |
| WO | WO 97/01087 | 1/1997 |
| WO | WO 98/34098 | 8/1998 |
| WO | WO 99/36766 | 7/1999 |
| WO | WO 00/22434 | 4/2000 |
| WO | WO 03/002985 | * 1/2003 |

* cited by examiner

*Primary Examiner*—Jeffrey R. Snay
(74) *Attorney, Agent, or Firm*—Seed IP Law Group PLLC

(57) ABSTRACT

A method of operating an analytical flow cell device comprising an elongate flow cell having a first end and a second end, at least two ports at the first end and at least one port at the second end, comprises introducing a laminar flow of a first fluid at the first end of the flow cell, and a laminar counter flow of a second fluid at the second end. Each fluid flow is discharged at the first end or the second end, and the position of the interface between the first and second fluids in the longitudinal direction of the flow cell is adjusted by controlling the relative flow rates of the first and second fluids. Also disclosed are a method of analyzing a fluid sample for an analyte, a method of sensitizing a sensing surface, and a method of contacting a sensing surface with a test fluid.

42 Claims, 4 Drawing Sheets

FLOW CELL METHOD

BACKGROUND OF THE INVENTION

1. Field of the Invention

The present invention generally relates to the control of a fluid flow over a surface, especially a sensing surface, within a flow cell of an analytical device and, more specifically, to the use of laminar flow cell techniques to position a fluid flow over desired surface areas within a flow cell.

2. Description of the Related Art

Flow cells are used extensively nowadays in a variety of analytical systems. Typically, the flow cell has an inlet opening, a flow channel and an outlet opening. A sample fluid to be investigated is introduced through the inlet opening, passes through the flow channel and leaves the flow cell through the outlet opening. In the flow channel, the sample fluid can be analyzed. The flow cell may have more than one inlet opening and optionally more than one outlet opening to permit desired manipulations of the flow pattern within the flow cell.

In one type of flow cell, the flow channel or channels contain a sensing surface, usually a substance layer to which a recognition element for an analyte in the sample is immobilized, typically a biochemical affinity partner to the analyte. When the analyte interacts with the recognition element, a physical or chemical change is produced on the sensing surface that can be detected by a detector, e.g. an optical, electrochemical or calorimetric detector. A flow channel may contain two or more sensing surfaces with different recognition elements.

The sensing surface or surfaces in the flow cell may be functionalized, or sensitized, in situ, i.e. within the flow cell. WO 90/05305 discloses a method for functionalizing a sensing surface having functional groups thereon by passing a reagent solution containing a bi- or polyfunctional ligand over the surface, the ligand having a function which immobilizes the ligand on the sensing surface and at least one more function which is exposed on the sensing surface for interaction with the analyte.

WO 99/36766 discloses methods and systems using hydrodynamic addressing techniques to allow immobilization of different ligands to discrete sensing areas within a single flow cell channel as well as to permit controlled sample delivery to such sensitized areas. In one embodiment, a so-called Y-cell having two inlet ports and one outlet port is used, wherein a laminar flow of a sample fluid (or sensitizing fluid in case of sensitization of the sensing surface) is provided adjacent to a laminar flow of a non-sensitizing fluid (e.g. a reference fluid) such that the fluids flow together over the sensing surface with an interface to each other. By adjustment of the relative flow rates of the two fluids the interface may be positioned laterally such that the sample fluid (or sensitizing fluid) contacts a desired discrete area of the sensing surface. In a variant, a so-called Ψ-cell having three inlet ports is used to sandwich the sample fluid (or sensitizing fluid) between two non-sensitizing fluid flows. A shortcoming of the methods and systems described in WO 99/36766 is, however, that selective contacting of a desired fluid with different areas of the sensing surface is only possible laterally, i.e. transversely to the flow path extension between the flow cell ends.

WO 97/01087 discloses a flow cell having an inlet opening for sample and an outlet opening. A further inlet opening for a reference fluid is provided which is positioned such that the reference fluid flows counter to the sample in the flow channel. In this way, the sample fluid may be kept away from the blocked volume occupied by the flowing reference fluid without the use of structural partitions in the flow channel. Typically, a detection layer containing sensitive recognition elements for an analyte extends the whole length of the flow cell channel, and the sample-free region of the flow channel can be used to generate a reference signal. However, the flow cell of WO 97/01087 has a fixed lengthwise extension of the sample region and the sample-free region, and requires that an outlet opening be located between the inlet openings for sample and reference fluid, respectively.

It would be desirable to be able to selectively and variably control the extension of a fluid flow in the longitudinal or normal direction of the flow cell. It would also be desirable to be able to use in this context a conventional type flow cell, such as the Y-cell or Ψ-cell mentioned above.

The present invention fulfills these needs and provides further related advantages.

BRIEF SUMMARY OF THE INVENTION

In brief, the present invention is directed to the control of a fluid flow over a surface within a flow cell using laminar flow cell techniques including a counter flow to position the fluid over a variable flow channel area extending from one end of the flow cell towards the other. More specifically, the interface between a laminar flow of a desired fluid and a laminar counter flow of another fluid, below often referred to as a "blocking fluid", may be positioned at a desired distance from the fluid inlet opening by controlling the laminar flows of the respective fluids.

Therefore, a first aspect of the present invention relates to a method of operating an analytical flow cell device comprising an elongate flow cell having a first end and a second end, at least two openings or ports at the first end and at least one opening or port at the second end. A laminar flow of a first fluid is introduced at the first end of the flow cell, a laminar counter flow of a second fluid is introduced at the second end of the flow cell, and each laminar fluid flow is discharged (independently of the other fluid flow) at the first end or the second end of the flow cell. The position of the interface between the first fluid and the second fluid in the longitudinal direction of the flow cell is controlled by adjusting the relative flow rates of the two fluids (or expressed otherwise, by adjusting the ratio of the flow of the first fluid to the combined discharge flow of the first fluid and the second fluid).

The first and second flow cell ends mentioned above are typically the upstream and downstream ends, respectively, of the flow cell with reference to the normal flow direction when a sample fluid is passed through the flow cell.

Preferably, the flow cell channel has at least one sensing surface on a wall surface within the flow cell located between the first (or upstream) end and the second (or downstream) end. The term "sensing surface" as used herein is to be construed broadly. The term includes, for example, not only a surface or surface layer that can interact with e.g. an analyte present in a fluid contacting the surface or the fluid per se, but also a surface that can be chemically or physically sensitized to permit the interaction to be sensed (detected), as well as a surface that can be chemically or physically activated, e.g. to permit subsequent sensitization thereof.

In one embodiment of the first-mentioned aspect of the invention, a laminar flow of a desired fluid is introduced through one port at the first end and discharged through a second port at the same end, and a blocking fluid is introduced from the second end of the flow cell. The blocking fluid may be discharged through the second port at the first end or, alternatively, at another port at the second end. Depending on the mutual flow rates of the two fluids, the interface between them, which extends substantially transversely to the longitudinal extension of the flow cell, may be positioned at different distances from the inlet/outlet end for the fluid.

One use of this embodiment is for selectively treating a desired portion of a sensing surface extending between the flow cell ends. In a common type of analytical flow cell, a sensing surface extends essentially the whole length between the ends of the flow cell, whereas only a (usually minor) part of the sensing surface defines a detection area or detection areas, i.e. an area or areas subjected to sensing by a detector, often located centrally in the flow cell. Selective treatment of a part of the sensing surface may be used for selectively contacting the upstream part (i.e. at the above-mentioned first end of the flow cell) of the sensing surface with a fluid containing an analyte-binding ligand to immobilize the ligand to the surface. If the sensing surface has a first detection area located within the immobilized surface region, and a second detection area further downstream outside the immobilized region, the upstream detection area may serve as a sensing area and the downstream detection area as a reference area.

Selective treatment of a sensing surface in a flow cell may also be used for partial deactivation of the sensing surface. In this case, the sensing surface may contain functional groups which need to be activated by an activating agent to form reactive groups capable of reacting with an analyte-specific ligand to be immobilized on the sensing surface. After activation of the sensing surface, the selective treatment described above may be used to treat the sensing surface area extending from the inlet port up to the vicinity of the detection area or areas with a deactivating agent in order to deactivate that part of the sensing surface. By deactivating the inlet portion of the sensing surface in this manner, the ligand to be immobilized on the sensing surface will not be attached to the sensing surface area preceding the detection area or areas. When sample is subsequently passed over the sensing surface, the deactivation performed will prevent analyte from being bound to the sensing surface on its way to the detection area or areas. In other words, the depletion of analyte in the sample fluid when passing through the flow cell to the detection area or areas will be minimized.

Another use of the above-mentioned embodiment is for obtaining rapid replacement of a fluid contacting a detection area within the flow cell with a fluid whose interaction with the sensing area is to be studied. This is, for example, useful for studying reaction kinetics. In a first state, the interface between the test fluid and the counter-flowing blocking fluid is positioned to be close to but not extending into or past the detection area. In a second state, the counter-flow is decreased or stopped and the test fluid is discharged at the second (downstream) end of the flow cell instead of at the first (upstream) end, permitting the test fluid to rapidly displace the blocking fluid and contact the detection area(s).

In another embodiment of the first-mentioned aspect of the invention, a laminar flow of a fluid is introduced at the first end and discharged through a port at the second end of the flow cell, and a counter flow of a blocking fluid is introduced through another port at the second end of the flow cell and discharged together with the first-mentioned fluid. Depending on the respective flow rates of the two fluids, the interface between them may be adjusted such that the blocking fluid covers a desired region at the second end of the flow cell. In an analogous manner to that described above for the first embodiment, one or more detection areas located on a sensing surface region covered by the blocking fluid may be prevented from contact with a ligand-containing fluid to thereby form a reference area or areas when the flow cell is subsequently used for analysis passing a sample fluid between the ends of the flow cell.

Another aspect of the present invention relates to a method of analyzing a fluid sample for an analyte, which comprises partially sensitizing a sensing surface within a flow cell using a laminar flow of a sensitizing fluid and a laminar counter flow of a blocking fluid according to the basic concept of the invention, and subsequently passing the fluid sample sequentially over the sensitized part and the non-sensitized part of the sensing surface.

Still another aspect of the present invention relates to a method of sensitizing a sensing surface, which comprises partially deactivating an activated sensing surface using a laminar flow of a deactivating fluid and a laminar counter flow of a blocking fluid as outlined above.

Yet another aspect of the present invention relates to a method of analysis, which comprises using a laminar flow of a test fluid and a laminar counter flow of a second fluid according to the basic concept of the invention to obtain rapid contacting of a sensing area within a flow cell with the test fluid. (The term "test fluid" is used herein in a broad sense and meant to include not only a fluid which through one or more constituents (analytes) or as such is capable of interacting with a sensing surface, but e.g. also a fluid that does not interact with the sensing surface, such as e.g. a buffer fluid, which may still, however, cause a change at the surface, e.g. dissociation of a bound analyte).

Other aspects of the invention also relates to sensitized sensing surfaces made by methods according to the invention.

In the specification and the appended claims, the singular forms "a", an and "the" are meant to include plural reference unless it is stated otherwise. Also, unless defined otherwise, technical and scientific terms used herein have the same meanings as commonly understood to a person skilled in the related to the invention.

It is also to be noted that the terms "comprising", "including" and "having" can be used interchangeably.

DETAILED DESCRIPTION OF THE INVENTION

Figure 1:
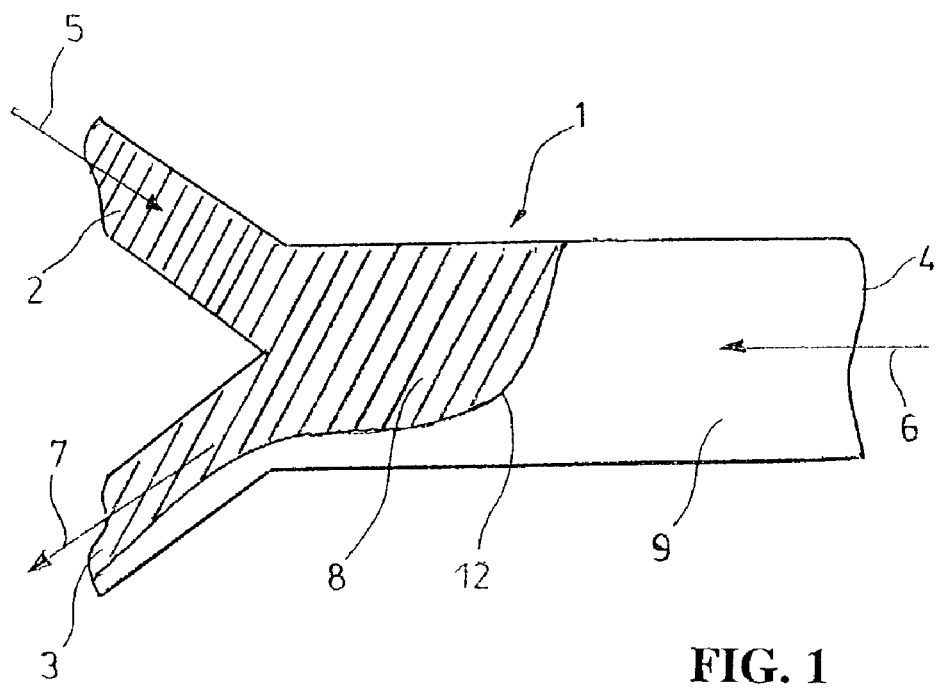
FIG. 1 schematically illustrates an embodiment of the method according to the present invention where a flow cell having two openings at one end and one opening at the opposite end is used.

As mentioned above, this invention is generally directed to the control of the fluid flow in the flow channel or flow channels of an analytical flow cell device, which usually has at least one sensing surface, using laminar flow techniques to control the fluid flow such that it can be made to occupy a variable portion of the flow channel length between the flow cell ends. While WO 99/36766 mentioned above (the entire disclosure of which is incorporated by reference herein) describes the controlled lateral movement of a fluid flow passing a flow cell from one end to the other using hydrodynamic addressing techniques, the present invention is directed to the control of the longitudinal spread of a fluid flow in the flow cell. Optionally, the present invention may be used in supplement to the methods and systems disclosed in WO 99/36766.

As in WO 99/36766, the configuration and dimensions of the flow cells to be used may vary widely depending upon the specific application and/or the specific detection method.

Representative detection methods include, but are not limited to, mass detection methods, such as piezoelectric, optical, thermo optical and surface acoustic wave (SAW) methods, and electrochemical methods, such as potentiometric, conductometric, amperometric and capacitance methods. With regard to optical detection methods, representative methods include those that detect mass surface concentration, such as reflection-optical methods, including both internal and external reflection methods, angle, wavelength or phase resolved, for example ellipsometry and evanescent wave spectroscopy (EWS), the latter including surface plasmon resonance (SPR) spectroscopy, Brewster angle refractometry, critical angle refractometry, frustrated total reflection (FTR), evanescent wave ellipsometry, scattered total internal reflection (STIR), optical wave guide sensors, evanescent wave-based imaging, such as critical angle resolved imaging, Brewster angle resolved imaging, SPR angle resolved imaging, and the like. Further, photometric methods based on, for example, evanescent fluorescence (TIRF) and phosphorescence may also be employed, as well as waveguide interferometers.

SPR spectroscopy may be mentioned as an exemplary commercially available analytical system to which the present invention may be applied. One type of SPR-based biosensors is sold by Biacore AB (Uppsala, Sweden) under the trade name BIACORE® (hereinafter referred to as "the BIACORE instrument"). These biosensors utilize a SPR based mass-sensing technique to provide a "real-time" binding interaction analysis between a surface bound ligand and an analyte of interest. An analytical system comprising a two-dimensional optical detector based on total internal or external reflection, e.g. an SPR detector, is disclosed in WO 98/34098 (the full disclosure of which is incorporated by reference herein).

However, any instrumentation or technique wherein a sample is brought into contact with a sensing surface within a flow cell under laminar flow conditions may benefit from this invention.

With regard to suitable flow cells for use in the practice of this invention, such flow cells may assume a number of forms, the design of which may vary widely depending upon the intended application and/or use. While several representative flow cells are disclosed herein for purpose of illustration, it should be recognized that any type of flow cell which is capable of contacting a liquid sample to a sensing surface under laminar flow conditions may be employed in the practice of this invention.

The basic principle of the present invention is schematically illustrated in FIG. 1. The flow cell 1 partially depicted in FIG. 1, referred to herein as an "Y-cell", has two openings 2, 3 (here shown as arms) at one end and one opening 4 at the opposite end of the flow cell. A sensing surface (not shown) is located between the two ends. A laminar flow of a desired fluid, indicated by arrow 5, is introduced through one of the two openings at the first end, here at 2, and a laminar counter flow of a (different) "blocking fluid", indicated by arrow 6, is introduced through the opening 4 at the opposite end of the flow cell. Both laminar fluid flows exit the flow cell through the second opening 3 at the first end. The discharge (typically suction) flow through the outlet opening 3, indicated by arrow 7, is considerably higher than the fluid flow 5 through inlet opening 2. As indicated by the hatched region 8 in FIG. 1, the desired fluid will only occupy the initial portion of the flow cell length (as seen from the first end). The remaining flow cell volume 9, including a small region extending through the outlet opening 3, is occupied by the blocking fluid which prevents the desired fluid from passing further into the flow cell. The spreading, or extension, of the pulse of the first fluid in the flow cell may be controlled by varying the ratio of the exit (suction) flow and the inlet flow of the second fluid. Thus, the higher the ratio, the larger part of the flow cell volume will be occupied by the second fluid.

Such variable length extension of a flow pulse may be used for different purposes. In one embodiment, a (e.g. bottom) wall of the flow cell supports a substance layer capable of reaction with a reagent solution, and the inventive procedure is used to react only a part of the substance layer with the reagent. One application of such a procedure is to provide a sensing area and a reference area arranged sequentially in the normal flow direction in a flow cell as will be described below with reference to FIG. 2.

Figure 2:
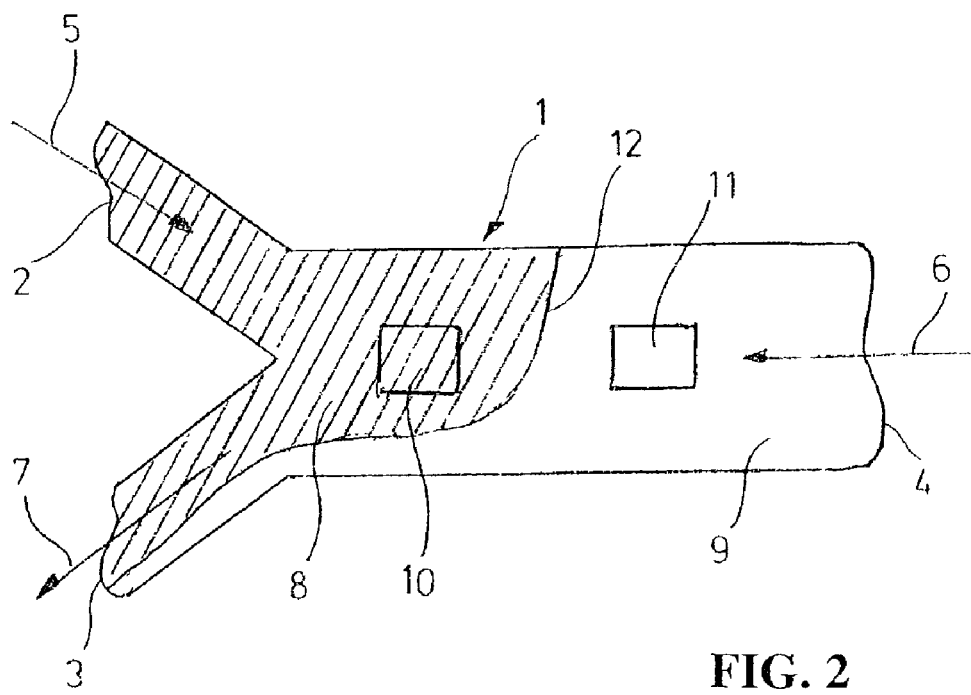
FIG. 2 schematically illustrates the method embodiment in FIG. 1 applied to a flow cell having two detection areas arranged at different distances from an inlet end.

In FIG. 2, where corresponding parts have the same reference numerals as in FIG. 1, the bottom wall of the flow cell supports a substance layer containing a recognition element, such as a receptor, for an analyte-specific ligand. Two detection areas 10, 11 are defined along the flow cell by the detection system used, for example an optical detection system. First, a flow of an inert fluid (i.e. one that does not react with the substance layer) is passed through the flow cell, being introduced through the opening 4 and discharged through at least one of the openings 2, 3. Then, a ligand-containing fluid 5 is introduced via opening 2 and discharged via opening 3, such that the ligand-containing fluid volume 8 extends past the first detection area 10 but not up to the second detection area 11, the interface 12 between the two fluids thus being positioned between the detection areas 10 and 11. Thereby, the detection area 10 will support the ligand, whereas the detection area 11 will not. When subsequently using the flow cell for analyzing a sample flow for an analyte introduced through, for example, one (or both) of the openings 2, 3 and discharged via the opening 4, the detection area 10 will form a sensing area, and the detection area 11 will form a reference area.

Figure 3:
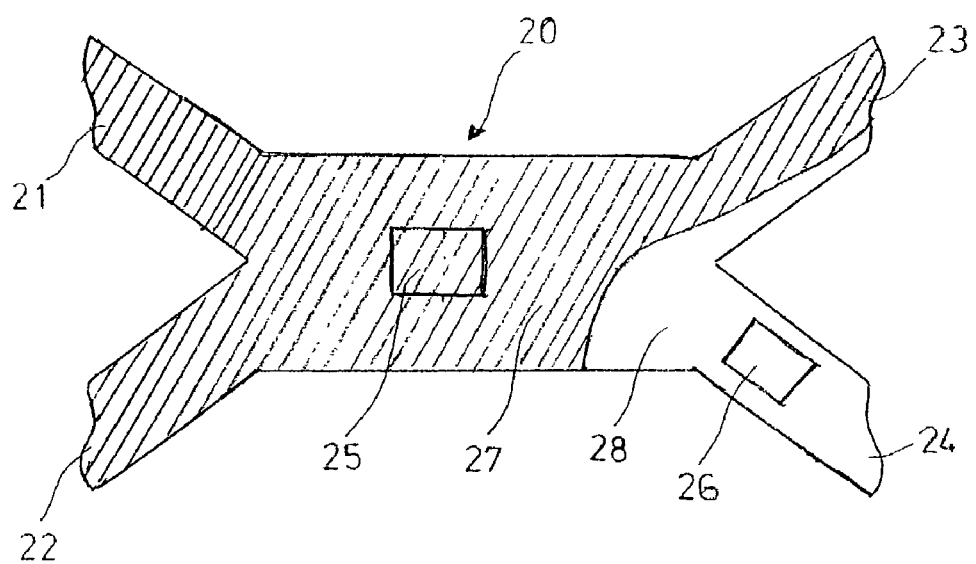
FIG. 3 schematically illustrates another embodiment of the invention using a flow cell having two openings at each end and two detection areas arranged at different distances from the ends.

Another embodiment of providing sequentially arranged sensing and reference areas in a flow cell is shown in FIG. 3. A flow cell 20, which may be characterized as a "double Y-cell", has two inlet arms 21, 22, and two outlet arms 23, 24. In the same way as in FIG. 2, the bottom wall of the flow cell supports a substance layer containing a recognition element for a ligand, and two detection areas are defined by the detection system used. One detection area 25 is located centrally in the flow cell, and the other detection area 26 is located in one of the outlet arms, here 24. A laminar flow of buffer fluid is first passed through the flow cell, entering via the inlets 21, 22 and the outlet 24, and exiting via the outlet 23. Then, the buffer flow through inlets 21, 22 (but not through outlet 24) is replaced by a laminar flow of ligand-containing fluid. This will result in the ligand-containing fluid occupying the hatched region 27 including the detection area 25, while the buffer fluid entering via outlet 24 will occupy the "blocked" region 28. The detection area 25 will thus react with and support the ligand, whereas the detection area 26 will not be contacted with ligand. When subsequently using the flow cell for analysis of an analyte-containing sample fluid, the sample fluid may be introduced through one (or both) of the inlet arms 21, 22, and discharged through outlet 24 (and optionally also through outlet 23). The detection area 25 will then serve as a sensing area and the detection area 26 as a reference area.

Figure 4:
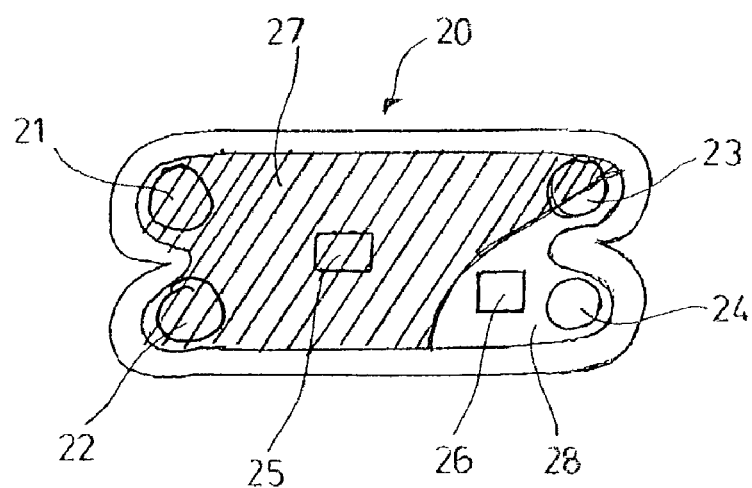
FIG. 4 schematically illustrates a variant of the embodiment in FIG. 3.

FIG. 4 illustrates a variant design of the embodiment in FIG. 3. Corresponding parts are indicated by the same reference numerals as in FIG. 3. In FIG. 4, the inlet arms are replaced by ports 21, 22 opening within the flow cell 20, and the outlet arms are replaced by ports 23, 24, also within the flow cell. By controlling the ratio between the laminar flows of the ligand-containing fluid entering via ports 21, 22 and the buffer fluid entering via port 24, the blocked region occupied by the buffer fluid may be made to include the detection area 26.

It is readily appreciated by the skilled person that the procedures of the invention outlined above may be carried out with many other types of flow cells, such as, e.g., the so-called "Ψ-cell" (described in the above-mentioned WO 99/36766) which has three inlets and one outlet.

The present invention may advantageously be used in conjunction with the hydrodynamic addressing techniques disclosed in the above-mentioned WO 99/36766, as will be described below.

Figure 5A:
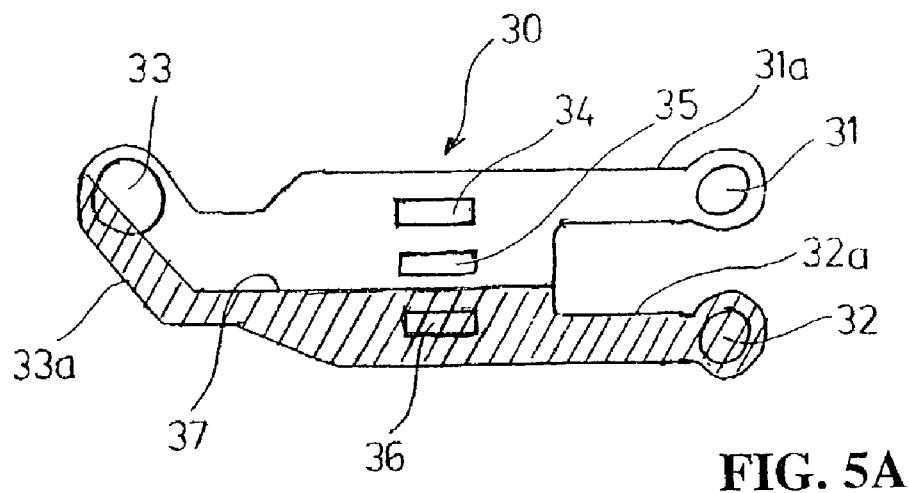
FIGS. 5A to 5C schematically illustrate embodiments of the invention where a flow cell having three parallel detection areas is used.
Figure 5B:
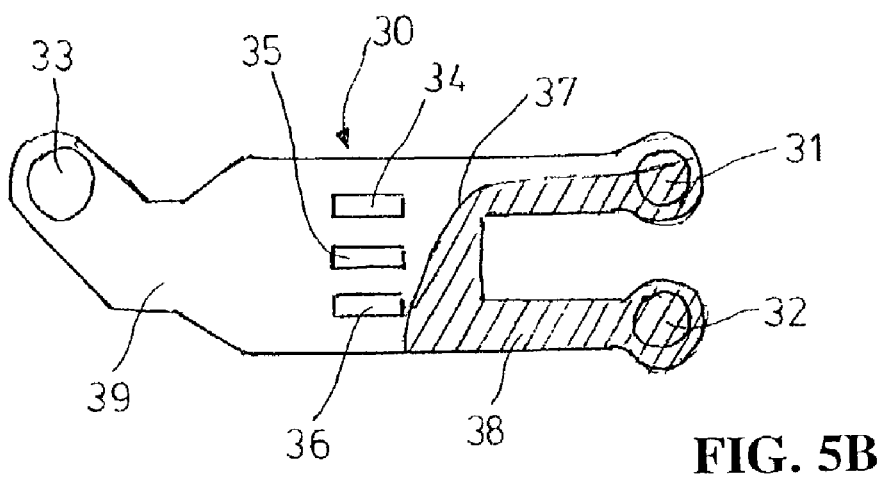
Figure 5C:
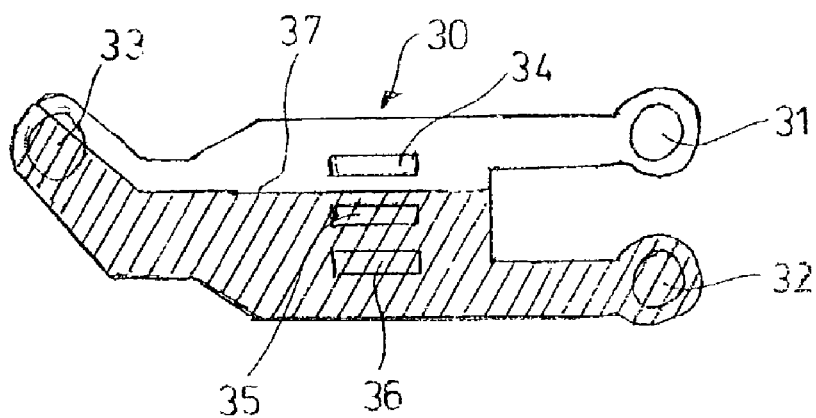

FIGS. 5A to 5C illustrate a flow cell 30 of the "Y-cell" type having two inlet ports 31 and 32 (at the ends of respective inlet arms 31a and 32a), and one outlet port 33 (at the end of an outlet arm 33a). Centrally in the flow cell are located three detection areas 34, 35, 36. The whole bottom wall of the flow cell 30 (the whole flow cell surface shown in the supports a material layer containing a functional group capable of being activated by an activating agent. This material layer may, for example, be a carboxymethyl-modified dextran gel, wherein the carboxyl groups may be activated by, for instance, N-hydroxysuccinimide (NHS) and N-ethyl-N-dimethylaminopropyl carbodiimide (EDC) to form reactive N-hydroxysuccinimide ester groups.

With reference to FIG. 5A, according to the hydrodynamic addressing techniques described in the above-mentioned WO 99/36766, a laminar flow of buffer is introduced through inlet port 31 and a laminar flow of a fluid containing activating agent is introduced through inlet port 32. The laminar flow rates of the two fluids are adjusted such that the interface 37 between the two fluids is between the detection areas 35 and 36, the activating fluid covering the hatched region in FIG. 5A. This means that only detection area 36 will be contacted by activating agent and activated whereas detection areas 34 and 35 will not.

The detection area 36 is then to be reacted with a ligand-containing solution such that it may be used as a sensing area when an analyte-containing sample is passed through the flow cell. However, before reacting the detection area 36 with the ligand-solution, the present invention concept is used to deactivate the inlet portion of the flow cell 30 up to the vicinity of the detection area 36. In this way, the material on the flow cell bottom upstream of the detection area 36 will not contain activated reactive groups and will therefore not bind ligand. This means in turn that the depletion of analyte on its way to the detection area 36 will be minimized when subsequently passing a sample flow through the flow cell from the inlet end to the outlet end.

To achieve the desired deactivation, now referring to FIG. 5B, a laminar flow of a buffer fluid is introduced through outlet port 33 to exit the flow cell via inlet port 31. A laminar flow of deactivating agent is then introduced through port 32 and discharged through inlet port 31, such that a laminar flow of buffer fluid introduced through outlet port 33 is maintained. The ratio of the laminar inlet flow through inlet port 32 and the laminar outlet flow through port 31 is adjusted such that the interface 37 between the flows of deactivating fluid and buffer fluid is positioned close to the detection areas 34 to 36, such that the deactivating fluid passes near but does not spread into the detection areas. The flow cell region occupied by of the deactivating fluid in the flow cell 30 is illustrated by the hatched region 38 in FIG. 5B. The flow cell volume blocked by the buffer fluid flow is indicated by reference numeral 39.

The same procedure as just described above with reference to FIGS. 5A and 5B may then be applied to the detection area 34 to immobilize a different ligand thereto after deactivation of the flow cell inlet region upstream of the detection area 34. The detection areas 34 and 36 will thereby form sensing areas while the intermediate detection area 35 will form a reference area. It is appreciated that such formation of a number of parallel detection areas by a hydrodynamic addressing technique in the present type of flow cell (such as Y-cell, Ψ-cell etc.) permits effective use of the sensing surface area of the flow cell.

To analyze a sample solution for ligand-specific analytes, a laminar fluid flow of the sample solution may be introduced through one (or both) of the inlet ports 31, 32 and discharged via outlet port 33, addressing all three detection areas 34 to 36 in the flow cell simultaneously.

Alternatively, the sample solution may be analyzed using the hydrodynamic addressing technique described in WO 99/36766. With reference to FIG. 5C, buffer fluid is first passed through the flow cell 30. A laminar flow of the sample solution is then introduced through inlet port 32, and a laminar flow of buffer is introduced through inlet port 31. The laminar flow rates of the two fluids are adjusted to bring the sample flow (the hatched region in FIG. 5C) into contact with the detection areas 35 and 36 by placing the fluid interface 37 between the reference area 35 and the sensing area 34. Thereby the sample fluid will contact the sensing area 36 and the reference area 35 and analyte specific to the ligand immobilized on sensing area 36 will bind to the analyte. To address the detection areas 34 and 35, the same (or another) sample fluid is introduced via inlet port 31 and buffer fluid via inlet port 32, and the interface 37 is moved to a location between the detection areas 35 and 36.

It is readily appreciated that the hydrodynamic addressing techniques described in WO 99/36766 may also be used together with the present invention to provide a sensing surface having two or three parallel sensing areas (e.g. as in FIGS. 5A to 5C) and one or more reference areas located downstream (e.g. as in FIGS. 2 to 4).

In a particular type of flow cells, one or more flow cells are formed by pressing a plate or chip with one or more sensing surfaces, below referred to as a sensor unit, in contact with an element or block having one or more open channels therein. Such a flow cell device is described in, for instance, WO 90/05245 (the disclosure of which is incorporated by reference herein) and is also used in the commercial BIACORE instrument mentioned above. Using a detachable sensor unit like that will permit e.g. sensitization (including optional activation and deactivation) according to the invention in one or more flow cells and after removal of the sensor unit, analysis with the sensor unit in another analytical device (which could, of course, also be another flow cell device).

The present invention may also be used to cause a rapid change or shift of a fluid contacting one or more sensing areas in a flow cell. While WO 99/36766 discloses a rapid shift of a contacting fluid by lateral movement of the interface between two different fluids flowing through the flow cell, the present invention permits such a shift by movement of the interface between the fluids in the longitudinal direction of the flow cell. This may be illustrated by reference to FIG. 5B. Assume that the sensing areas 34 and 36 support ligands capable of specifically reacting with an analyte in a sample. A laminar flow of the sample is introduced through the port 32 and a laminar buffer flow is introduced through the port 33. Both the sample flow and the buffer flow are discharged through the port 31, the ratio between the sample flow and the buffer flow being adjusted to position the interface 37 near but not within the detection areas 34 to 36, such that the sample flow 38 (the hatched region in FIG. 5B) is not in contact therewith. The sample and buffer flow rates are then adjusted to move the interface 37 to a position (not shown in FIG. 5B) on the other (upstream) side of the detection areas 34 to 36, thus bringing the sample flow into contact with the detection areas. Alternatively, rather than moving the interface 37 as above, the interface may be removed by filling the whole flow cell with sample by closing the port 31, stopping the buffer flow and discharging the sample flow through the port 33.

It is appreciated that the rise and fall times are limited only by the movement of the interface from a first position not in contact with the detection areas to a second position such that the sample flow is in contact with the detection areas. The volume of sample required to move the interface from the first to the second position is a fraction of the volume of the flow cell itself. Thus, instead of shifting from buffer flow to sample flow with valves at some distance from the sensing area, the interface can be moved with only a fraction of the volume of the flow cell. Since the rise time is proportional to the volume that has to be displaced, a tenfold decrease in volume reduces the rise time by about 10 fold. Similar advantages are achieved with shorter fall times.

Such fast rise and fall times are of necessity when measuring fast reaction kinetics, for example, when studying association and dissociation. In one embodiment, an analyte may be passed over a sensitized sensing area(s). The sample flow may then be displaced from contact with the sensitized sensing area(s), and the dissociation rate can be detected. Alternatively, a sample flow may be rapidly displaced onto a sensitized sensing area(s), thereby allowing for the detection and analysis of association kinetics.

A variant embodiment of the invention to achieve rapid fluid shifts will be described below with reference to FIGS. 6A and 6B. This embodiment utilizes a flow cell 40 which like the flow cell in FIGS. 3 and 4 has two openings 41, 42 at one end and two openings 43, 44 at the other end. Each opening 41 to 44 is associated with a respective valve (not shown) which opens or closes the opening. A number of detection areas (here three) 45a to 45c are located centrally in the flow cell 40.

Figures 6A, 6B:
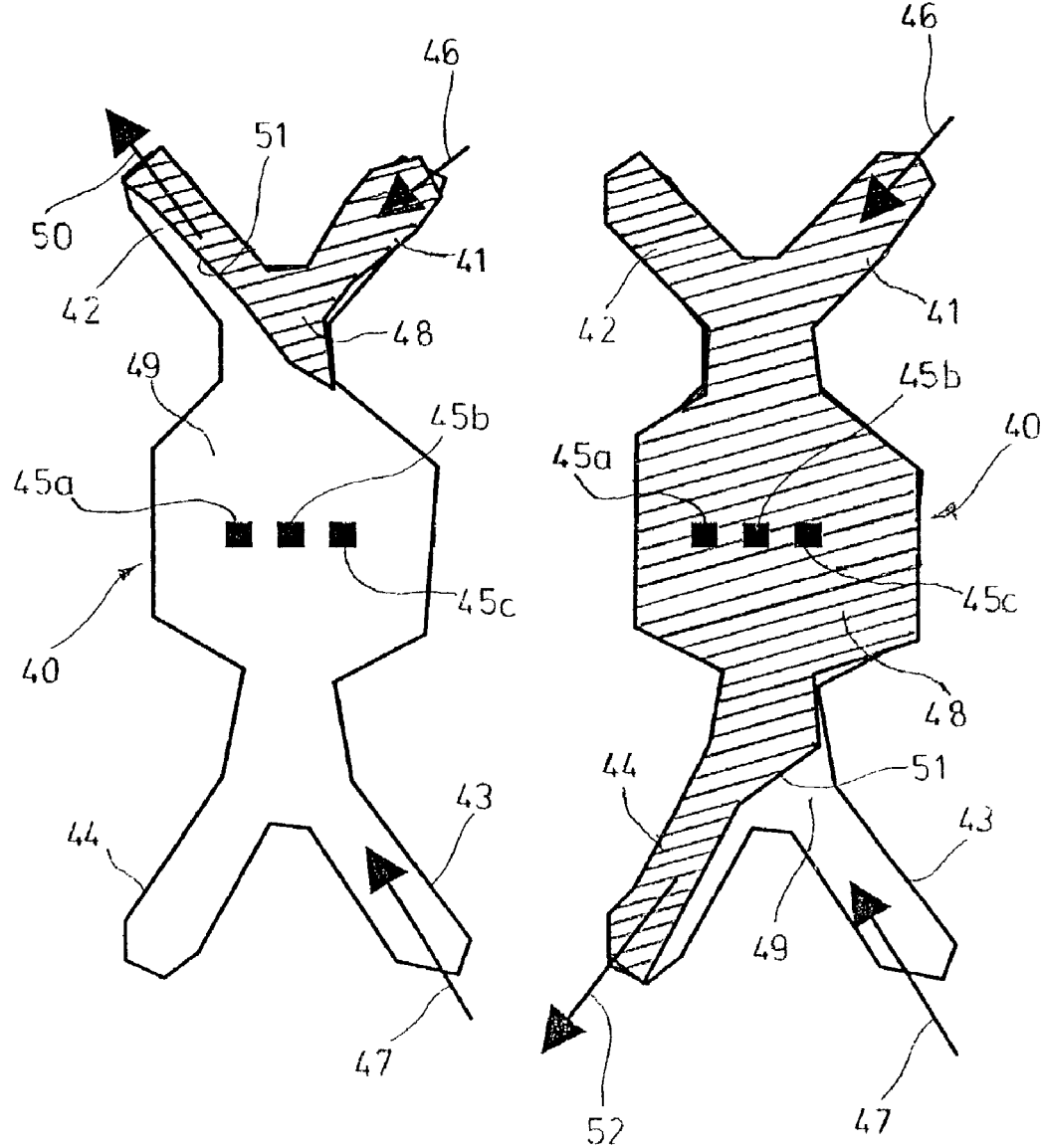
FIGS. 6A and 6B schematically illustrate still another embodiment of the invention where a flow cell having two openings at each end is used.

In FIG. 6A, a laminar flow of e.g. a sample fluid, indicated by arrow 46, is introduced through the opening 41, and laminar flow of e.g. buffer, indicated by arrow 47, is introduced through the opening 43. Both fluid flows are discharged through the opening 42, indicated by arrow 50. The sample flow 48 (the hatched region in FIG. 5A) and the buffer flow 49 together form a combined flow with an interface 51 between them. In this state of the flow cell 40, the detection areas 45a–c are in contact only with the buffer flow.

The state of the flow cell 40 is then changed to that shown in FIG. 6B by closing the valve associated with the opening 42 and opening the valve associated with the opening 44. This causes the sample flow and the buffer flow to exit the flow cell through the opening 44 in a combined flow, indicated by arrow 52, the interface 51 being displaced towards the opposite end of the flow cell 40, such that only the sample flow (the hatched region in FIG. 6B) contacts the detection areas 45a–c. Thus, by opening the valve associated with the opening 44 and closing the valve associated with the opening 42, or vice versa, a rapid shift of the fluid contacting the detection areas 45a–c may be obtained. Depending on the detailed design of the flow cell 40, it will usually be necessary to also regulate the individual flow rates of the buffer and sample flows, respectively.

In order to achieve the desired fluid shift as rapidly as possible, the interface 51 between the two laminar fluid flows is preferably positioned close to the row of detection areas 45a–c in FIG. 6A but not in contact therewith when a subsequent rapid contact with sample is desired (e.g. for studying the association of an analyte in the sample to a surface-bound ligand), and close to the row of detection areas 45a–c but on the opposite side thereof when a subsequent rapid contact with buffer is desired (e.g. for studying the dissociation of analyte from surface-bound ligand).

It is appreciated that with the procedure described above, the "dead volume" of the flow cell 40 will be very low and be reduced to only a part of the flow cell volume.

In the non-limiting Example following further below in order to illustrate the present invention further, a BIACORE instrument is used. As mentioned above, the BIACORE instrument is based on surface plasmon resonance (SPR). The analytical data is provided in the form of a sensorgram which plots the signal in resonance units (RU) as a function of time. A signal of 1,000 RU corresponds to the binding of about 1 ng of analyte per $mm^2$. A detailed discussion of the technical aspects of the BIACORE instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the BIACORE instruments may be found in U.S. Pat. No. 5,492,840. The full disclosures of the above-mentioned U.S. patents are incorporated by reference herein.

EXAMPLE 1

Deactivation of an activated inlet area of a flow cell to increase the mass transport to a sensing area A BIACORE S51® instrument (Biacore AB, Uppsala, Sweden) was used. The instrument includes a Y-channel flow cell of the type illustrated in FIGS. 5A to 5C. As sensor chip was used Sensor Chip CM5 (Biacore AB), which supports a gold surface with a covalently linked carboxymethyl-modified dextran polymer hydrogel. The optical system measures three detection spots located centrally on the sensing surface forming one channel wall of the flow cell.

1. Materials

Ligand: Biotin-jeffamine conjugate, Mw 374.5 (made in-house), 2 mM, 1.75 mg in 2386 µl of 10 mM borate, pH 8.5

Analyte: Biotin-antibody (from Biotin Kit, Biacore AB)

Coupling reagent: Amine coupling kit (Biacore AB), EDC/NHS (N-ethyl-N-dimethylaminopropylcarbodiimide and N-hydroxysuccinimide)

Drive buffer: PBS pH 7.2

Deactivating reagent: Ethanolamine

2. A. Sensitization of sensor chip CM5—Method 1 (prior art)

The sensor chip was first activated by injection of EDC/NHS for 420 s at a flow rate of 30 µl/min. Ligand, diluted 1:2 in borate buffer, was then injected for 140 s at a flow rate of 10 µl/min. After the immobilization of the ligand, ethanolamine was injected for 7 min at 30 µl/min to deactivate all activated sites that had not bound to ligand. Analyte, diluted 1:10 in PBS, was then injected for 120 s at 20 µl/min and the uptake of analyte at the detection spots was measured.

B. Sensitization of sensor chip CM5—Method 2 (method of the invention)

The sensor chip was first activated by injection of EDC/NHS for 420 s at a flow rate of 30 µl/min. The flow cell area preceding the detection spots was then selectively deactivated according to the procedure of the present invention as described above with reference to FIG. 5B, by injecting for 60 s ethanolamine at 21 µl/min and a counter flow of buffer at 40 µl/min. Ligand, diluted 1:2 in borate buffer, was then injected for 140 s at a flow rate of 10 µl/min, and activated sites that had not bound to ligand were deactivated by ethanolamine injection for 7 min at 30 µl/min. Analyte, diluted 1:10 in PBS, was then injected for 120 s at 20 µl/min and the uptake of analyte at the detection spots was measured.

3. Results

| Sensitization method | Uptake |
|---|---|
| Normal (Method 1) | 262 RU |
| Deactivated inlet part of flow cell (Method 2) | 447 RU |
| Ratio (deact./normal) | 1.71 |

From the above results it is seen that deactivation of the activated inlet area (up to the detection spots) in the flow cell, which prevents immobilization of ligand, increases the mass transport by approximately 70% in the present example. It may therefore be concluded that deactivation of all active area/volume before the detection spots (detection areas/detection volumes) minimizes the depletion of analyte. It is further apparent that use of this deactivation technique will permit the positioning of inlet channels having an "active surface" at an arbitrary distance from detection spots or detection areas or detection volumes.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method of operating an analytical flow cell device comprising an elongate flow cell having a first end and a second end, at least two ports at the first end and at least one port at the second end, which method comprises introducing a laminar flow of a first fluid at the first end of the flow cell, introducing a laminar counter flow of a second fluid at the second end of the flow cell, discharging each laminar fluid flow at the first end or the second end of the flow cell, and adjusting the position of the interface between the first fluid and the second fluid in the longitudinal direction of the flow cell by controlling the relative flow rates of the first fluid and the second fluid.

2. The method according to claim 1, wherein the first fluid is introduced through a first port at the first end of the flow cell and discharged through a second port at the first end.

3. The method according to claim 2, wherein the flow of the first fluid and the counter flow of the second fluid are both discharged through a port at the first end.

4. The method according to claim 1, wherein the flow cell is selected from a Y-type flow cell and a ψ-type flow cell.

5. The method according to claim 1, wherein the flow cell has at least two ports at the second end and the flow of the first fluid and the flow of the second fluid are discharged through one of the ports at the second end.

6. The method according to claim 1, wherein the flow cell has at least one sensing surface on a wall surface located between the first end and the second end of the flow cell.

7. The method according to claim 6, wherein the first fluid is capable of reacting with the sensing surface or surfaces, and the second fluid does not react with the sensing surface or surfaces.

8. The method according to claim 6, wherein the second flow is capable of reacting with the sensing surface or surfaces, and the first fluid does not react with the sensing surface or surfaces.

9. The method according to claim 6, wherein the at least one sensing surface comprises at least one detection area at a first distance from the first end of the flow cell and at least one detection area at a second, greater distance from the first end of the flow cell, and wherein the interface between the flow of the first fluid and the flow of the second fluid is adjusted to be at a position between the first distance and the second distance from the first end of the flow cell, such that the first fluid contacts the detection area or areas at the first distance and the second fluid contacts the detection area or areas at the second distance from the first end of the flow cell.

10. The method according to claim 9, wherein the at least one detection area at the first distance is an analyte-binding sensing area and the at least one detection area at the second distance is a reference area.

11. The method according to claim 7, wherein the at least one sensing surface comprises at least one detection area between the first end and the second end of the flow cell, and wherein the interface between the flow of the first fluid and the flow of the second fluid is adjusted to be at a position between the first end and the at least one detection area, such that the first fluid contacts a sensing surface region extending from the first end substantially up to the at least one detection area.

12. The method according to claim 11, wherein the at least one sensing surface is chemically activated, and the first fluid contains a deactivating agent, such that the sensing surface region contacted by the first fluid is deactivated.

13. The method according to claim 1, wherein the flow cell comprises at least one detection area between the first end and the second end of the flow cell, and wherein, in a first state, the interface is adjusted to be at a position between the first end and the at least one detection area, and, in a second state, the interface between the first fluid and the second fluid is moved to a position between the at least one detection area and the second end of the flow cell, such that the first fluid is brought in contact with the at least one detection area.

14. The method according to claim 13, wherein, in the first state, the interface is adjusted such that the first fluid contacts a sensing surface region extending from the first end substantially up to the at least one detection area.

15. The method according to claim 1, wherein the flow cell has two openings at the second end and at least one detection area between the first end and the second end, and wherein, in a first state, the first fluid is introduced through a first opening at the first end, the second fluid is introduced through a first opening at the second end, and each fluid flow is discharged at a second opening at the first end of the flow cell, such that the interface between the two fluid flows is at a position between the first end and the at least one detection area, and in a second state, the first fluid is introduced through the first opening at the first end of the flow cell, the second fluid is introduced through the first opening at the second end, and each fluid flow is discharged through a second opening at the second end, such that the interface between the two fluids is at a position between the at least one detection area and the second end of the flow cell.

16. The method according to claim 15, wherein a change from the first state to the second state comprises stopping the fluid flow through the second opening at the first end and discharging the two fluid flows through the second opening at the second end.

17. The method according to claim 15, wherein a change from the second state to the first state comprises stopping the fluid flow through the second opening at the second end and discharging the two fluid flows through the second opening at the first end.

18. The method according to claim 1, wherein the flow cell device comprises a fluid channel element having at least one channel in a flat surface thereof, and a plate member having at least one sensing surface on a face thereof, which plate member is adapted one to be detachably pressed against the fluid channel element to form with each channel a flow cell containing a sensing surface.

19. A method of sensitizing a sensing surface arranged to be passed by a fluid flow within a flow cell, comprising the steps of:
passing a laminar flow of an activating fluid through the flow cell to chemically activate the sensing surface,
passing a laminar flow of a deactivating fluid and a laminar counter flow of a blocking fluid over the sensing surface with an interface to each other, and adjusting the flow rates of the two fluids such that the deactivating fluid selectively contacts and deactivates a predetermined region of the activated sensing surface extending from one end of the flow cell, and
selectively sensitizing the activated part of the sensing surface by passing a laminar flow of a sensitizing fluid over the sensing surface.

20. The method according to claim 19, wherein the flow cell has a first end and a second end and the interface between the deactivating fluid and the blocking fluid extends substantially transversely to the extension of the flow cell between the two ends thereof.

21. The method according to claim 19, wherein the sensitizing step comprises:
providing a laminar flow of a first, sensitizing fluid and a laminar flow of a second fluid adjacent to the flow of the sensitizing fluid such that the two fluids flow together over the sensing surface with an interface to each other, at least the sensitizing fluid being capable of sensitizing the sensing surface, and
adjusting the relative flow rates of the sensitizing fluid and the second fluid to position the interface such that the sensitizing fluid contacts a discrete sensing area of the sensing surface for selective sensitization thereof.

22. The method according to claim 21, wherein the flow cell has a first end and a second end and the interface between the sensitizing fluid and the second fluid extends substantially in parallel to the extension of the flow cell between the first end and the second end thereof.

23. A sensitized sensing surface prepared according to the method of claim 19.

24. A method of analyzing a fluid sample for an analyte, comprising the steps of:
passing a laminar flow of an activating fluid through a flow cell having a sensing surface to chemically activate the sensing surface,
passing a laminar flow of a deactivating fluid and a laminar counter flow of a blocking fluid over the sensing surface with an interface to each other, and adjusting the flow rates of the two fluids such that the deactivating fluid selectively contacts and deactivates a predetermined region of the activated sensing surface extending from one end of the flow cell,
selectively sensitizing the activated part of the sensing surface by passing a laminar flow of a sensitizing fluid over the sensing surface, and
contacting the sensitized area with the fluid sample, and detecting interaction between the analyte and the detection area.

25. The method according to claim 24, which comprises detecting interaction events at one or more detection areas by an optical sensor.

26. The method according to claim 25, wherein the optical sensor is based on evanescent sensing, especially surface plasmon resonance.

27. A method of analyzing a fluid sample for an analyte, comprising the steps of:
providing a flow cell having a first end and a second end, and a sensing surface on a wall surface within the flow cell,
introducing a laminar flow of a sensitizing fluid at the first end of the flow cell, introducing a laminar counter flow of a blocking fluid at the second end of the flow cell, discharging each laminar fluid flow at the first end or at the second end of the flow cell, and adjusting the position of the interface between the sensitizing fluid and the blocking fluid such that the sensitizing fluid contacts a first portion of the sensing surface and the blocking fluid contacts a second portion of the sensing surface to selectively sensitize the first portion of the sensing surface,
introducing a laminar flow of the fluid sample at the first end of the flow cell and discharging the flow of fluid sample at the second end of the flow cell, such that the sample flow sequentially passes the sensitized portion of the sensing surface and the non-sensitized portion of the sensing surface, and detecting interaction of the analyte with the sensitized and non-sensitized portions of the sensing surface.

28. A method of analysis, comprising the steps of:
providing a flow cell having a first end and a second end, and at least one sensing area on a wall surface within the flow cell spaced from the first end of the flow cell,
introducing a laminar flow of a test fluid at the first end of the flow cell, introducing a laminar counter flow of a second fluid at the second end of the flow cell, and discharging each fluid flow at the first end or at the second end of the flow cell, such that an interface is formed between the two fluids which extends substantially transversely to the extension of the flow cell between the ends thereof,
in a first state, setting the relative flow rates of the test fluid and the second fluid to position the interface such that the test fluid is at a position between the first end and the at least one sensing area,
in a second state, changing the relative flow rates of the laminar fluid flows such that the interface is at a position between the at least one sensing area and the second end of the flow cell, and
determining the influence of the test fluid on the at least one sensing area.

29. The method according to claim 28, wherein, in the first state, the interface is positioned such that the test fluid extends from the first end substantially up to but not into contact with the at least one sensing area.

30. The method according to claim 28, wherein, in the second state, the interface is positioned such that the second fluid extends from the second end substantially up to but not into contact with the at least one sensing area.

31. The method according to claim 28, wherein the test fluid contains an analyte and the association of the analyte to a sensing area is determined.

32. The method according to claim 31, wherein the test fluid contains an analyte and the association of the analyte to a sensing area is determined.

33. The method according to claim 31, wherein the test fluid is analyte-free and the dissociation of an analyte from a sensing area is determined.

34. The method according to claim 28, wherein the test fluid is analyte-free and the dissociation of an analyte from a sensing area is determined.

35. A method of analysis, comprising the steps of:
providing a flow cell having a first end and a second end, each end having two openings, and at least one sensing area on a wall surface within the flow cell spaced from the ends of the flow cell,
in a first state, introducing a laminar flow of a test fluid through a first opening at the first end of the flow cell, introducing a laminar counter flow of a second fluid through a first opening at the second end of the flow cell, and discharging each fluid flow through a second opening at the first end, such that an interface between the two laminar fluid flows is formed at a position between the first end of the flow cell and the at least one sensing area,
in a second state, introducing a laminar flow of the test fluid through the first opening at the first end of the flow cell, introducing a laminar counter flow of the second fluid through the first opening at the second end of the flow cell, and discharging each fluid flow through a second opening at the second end, such that the interface between the two laminar fluid flows is at a position between the second end of the flow cell and the at least one sensing area, changing between at least one of (i) the first state and the second state, and (ii) the second state and the first state, and
determining the influence of the change on the at least one sensing area.

36. The method according to claim 25, wherein, in the first state, the interface is positioned such that the test fluid extends from the first end substantially up to but not into contact with the at least one sensing area.

37. The method according to claim 25, wherein, in the second state, the interface is positioned such that the second fluid extends from the second end substantially up to but not into contact with the at least one sensing area.

38. The method according to claim 25, wherein the change from the first state to the second state comprises closing the second opening at the first end and opening the second opening at the second end.

39. The method according to claim 25, wherein the change from the second state to the first state comprises closing the second opening at the second end and opening the second opening at the first end.

40. An analytical method comprising the steps of:
providing a flow cell device comprising a fluid channel element having at least one channel in a flat surface thereof, and a plate member having at least one sensing surface on a face thereof, which plate member is adapted to be detachably pressed against the fluid channel element to form with each channel a flow cell containing a sensing surface,
independently treating the sensing surface of at least one flow cell by introducing at the first end of the flow cell a laminar flow of a first fluid capable of reacting with the sensing surface, introducing at the second end of the flow cell a laminar counter flow of a second fluid that does not react with the sensing surface, discharging each laminar fluid flow at the first end or the second end of the flow cell, and adjusting the position of the interface between the first fluid and the second fluid between the flow cell ends by controlling the relative flow rates of the first fluid and the second fluid to selectively react at least one sensing area of the sensing surface of the flow cell, and
moving the plate member from the flow cell device to an analytical device and subjecting the treated sensing surface or surfaces to an analytical procedure.

41. A method of chemically treating a surface area within a flow cell, comprising the steps of:
providing a flow cell having a first end and a second end,
introducing a laminar flow of a treating fluid at the first end of the flow cell,
introducing a laminar counter flow of a blocking fluid at the second end of the flow cell,
discharging each laminar fluid flow at the first end or at the second end of the flow cell, such that the two fluids pass the flow cell with an interface between them, and
adjusting the relative flow rates of the two fluids such that the interface is positioned at a predetermined distance from the first end of the flow cell to selectively contact with the treating fluid a wall surface area within the flow cell extending the predetermined distance from the first end of the flow cell.

42. The method according to claim 41, wherein the wall surface area is part of a chemically active surface, and the treating fluid is capable of deactivating the active surface.

* * * * *

UNITED STATES PATENT AND TRADEMARK OFFICE
CERTIFICATE OF CORRECTION

PATENT NO. : 7,015,043 B2 Page 1 of 1
APPLICATION NO. : 10/184024
DATED : March 21, 2006
INVENTOR(S) : Håkan Roos et al.

It is certified that error appears in the above-identified patent and that said Letters Patent is hereby corrected as shown below:

Column 16
Line 6, "claim 25," should read as --claim 35,--.

Column 16
Line 10, "claim 25," should read as --claim 35,--.

Column 16
Line 14, "claim 25," should read as --claim 35,--.

Column 16
Line 18, "claim 25," should read as --claim 35,--.

Signed and Sealed this

Nineteenth Day of September, 2006

JON W. DUDAS
*Director of the United States Patent and Trademark Office*